US010376859B2

(12) United States Patent
Coloma González et al.

(10) Patent No.: US 10,376,859 B2
(45) Date of Patent: Aug. 13, 2019

(54) UREA PRODUCTION WITH BI-PRESSURIZED SYNTHESIS

(71) Applicant: STAMICARBON B.V., Sittard (NL)

(72) Inventors: Juan Coloma González, Sittard (NL); Luc Louis Maria Dieltjens, Sittard (NL); Johannes Henricus Mennen, Sittard (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 15/576,214

(22) PCT Filed: Mar. 30, 2017

(86) PCT No.: PCT/NL2017/050196
§ 371 (c)(1),
(2) Date: Nov. 21, 2017

(87) PCT Pub. No.: WO2017/171546
PCT Pub. Date: Oct. 5, 2017

(65) Prior Publication Data
US 2019/0015811 A1    Jan. 17, 2019

(30) Foreign Application Priority Data
Mar. 30, 2016   (EP) .................................. 16162901

(51) Int. Cl.
B01J 19/00     (2006.01)
B01J 19/18     (2006.01)
(Continued)

(52) U.S. Cl.
CPC .......... *B01J 19/1837* (2013.01); *B01D 5/006* (2013.01); *B01J 19/24* (2013.01); *C07C 273/04* (2013.01);
(Continued)

(58) Field of Classification Search
CPC ... B01D 3/00; B01D 3/06; B01D 3/14; B01D 5/00; B01D 5/0057; B01D 5/006;
(Continued)

(56) References Cited

U.S. PATENT DOCUMENTS

2010/0069631 A1*   3/2010   Zardi .................... C07C 273/12
                                                    544/222

FOREIGN PATENT DOCUMENTS

EP         1 491 526        12/2004
WO      WO-2013/104638      7/2013

OTHER PUBLICATIONS

International Search Report and Written Opinion for PCT/NL2017/050196, dated Jun. 6, 2017, 9 pages.
(Continued)

*Primary Examiner* — Natasha E Young
(74) *Attorney, Agent, or Firm* — Morrison & Foerster LLP

(57) ABSTRACT

The invention is directed to a urea plant with a high pressure synthesis section and a recovery section. The high pressure synthesis section comprises a reactor, a stripper and a condenser, wherein the reactor operates at a higher pressure than the stripper and the condenser. The plant further includes a compression unit between the condenser and the reactor. The compression unit utilizes mechanical energy recovered from a decompression unit positioned downstream of the stripper and upstream of the recovery section.

20 Claims, 3 Drawing Sheets

(51) Int. Cl.
*B01J 19/24* (2006.01)
*B01D 3/06* (2006.01)
*B01D 3/14* (2006.01)
*B01D 5/00* (2006.01)
*C07C 273/04* (2006.01)
*C07C 275/02* (2006.01)
*B01L 3/06* (2006.01)
*B01L 3/14* (2006.01)

(52) U.S. Cl.
CPC ...... *C07C 275/02* (2013.01); *B01D 2257/406* (2013.01); *B01D 2257/504* (2013.01); *B01J 2219/0004* (2013.01); *B01J 2219/00018* (2013.01); *B01J 2219/00038* (2013.01); *B01J 2219/00051* (2013.01); *B01J 2219/00162* (2013.01); *B01L 3/06* (2013.01); *B01L 3/14* (2013.01); *Y02P 20/582* (2015.11)

(58) Field of Classification Search
CPC .......... B01D 2257/40; B01D 2257/406; B01D 2257/50; B01D 2257/504; B01J 19/18; B01J 19/1812; B01J 19/1837; B01J 19/24; B01J 2219/00; B01J 2219/00002; B01J 2219/00018; B01J 2219/00027; B01J 2219/00038; B01J 2219/0004; B01J 2219/00049; B01J 2219/00051; B01J 2219/00162; C07C 273/00; C07C 273/02; C07C 273/04; C07C 275/00; C07C 275/02; Y02P 20/50; Y02P 20/58; Y02P 20/582

See application file for complete search history.

(56) References Cited

OTHER PUBLICATIONS

Meessen, "Urea," In: Ullmann's Encyclopedia of Industrial Chemistry, Wiley VCH-Verlag GmbH & Co. KGaA, Weinhwim, Germany (2010) vol. 37, 657-695.

* cited by examiner

UREA PRODUCTION WITH BI-PRESSURIZED SYNTHESIS

CROSS-REFERENCE TO RELATED APPLICATIONS

This application is the national phase of PCT application PCT/NL2017/050196, now WO 2017/171546, having an international filing date of 30 Mar. 2017, which claims benefit of European patent application No. 16162901.9 filed 30 Mar. 2016. The contents of the above patent applications are incorporated by reference herein in their entirety.

FIELD OF THE INVENTION

The invention is in the field of urea production, and particularly pertains to a urea stripping process. The invention particularly pertains to recovering energy in such a process. The invention also pertains to a urea production plant, and to revamping an existing urea production plant.

BACKGROUND OF THE INVENTION

Urea is generally produced from ammonia and carbon dioxide. It can be prepared by introducing an ammonia excess together with carbon dioxide at a pressure between 12 and 40 MPa and at a temperature between 150° C. and 250° C. into a urea synthesis zone. The resulting urea formation can be presented best in the form of two consecutive reaction steps, in the first step ammonium carbamate being formed according to the exothermic reaction:

$$2NH_3 + CO_2 \rightarrow H_2N\text{---}CO\text{---}ONH_4$$

after which the ammonium carbamate formed is dehydrated in the second step to give urea according to the endothermic equilibrium reaction:

$$H_2N\text{---}CO\text{---}ONH_4 \leftrightarrow H_2N\text{---}CO\text{---}NH_2 + H_2O$$

The extent to which these reactions take place depends among other things on the temperature and the ammonia excess used. The reaction product obtained in a urea synthesis solution substantially consists of urea, water, unbound ammonia and ammonium carbamate. The ammonium carbamate and the ammonia are removed from the solution and are generally returned to the urea synthesis zone.

In addition to the above-mentioned solution in the urea synthesis zone, a gas mixture is formed which consists of unconverted ammonia and carbon dioxide together with inert gases, the so called reactor off-gas. The urea synthesis section may comprise separate zones for the formation of ammonium carbamate and urea. These zones may also be combined in a single apparatus.

The invention pertains to a process for the preparation of urea according to a stripping process, as conducted in a urea stripping plant. Such a process is described in, inter alia, Ullmann's Encyclopedia of Industrial Chemistry, Vol. A27, 1996, pp 333-350.

In a urea stripping plant the decomposition of the ammonium carbamate that has not been converted into urea and the expulsion of the usual ammonia excess largely takes place at a pressure that is essentially almost equal to the pressure in the synthesis reactor. This decomposition and expulsion take place in one or more stripper(s) installed downstream of the reactor, possibly with the aid of a stripping gas such as, for example, carbon dioxide and/or ammonia, and with the addition of heat. It is also possible to apply thermal stripping. Thermal stripping means that use is made exclusively of the supply of heat to decompose ammonium carbamate and remove the ammonia and carbon dioxide present from the urea solution. The gas stream leaving a stripper contains ammonia and carbon dioxide which are condensed in a high-pressure condenser and then returned to the urea synthesis zone.

In a urea stripping plant the synthesis zone is operated at a temperature of 160-240° C. and preferably at a temperature of 170-220° C. The pressure in the synthesis reactor is 12-21 MPa, preferably 12.5-20 MPa, more preferably 13-16 MPa. In the art, these ranges are generally considered to represent "high pressure" (as also used in connection with a conventional "High Pressure Carbamate Condenser"). The gross ammonia to carbon dioxide molar ratio (gross N/C ratio) in the urea synthesis zone of a stripping plant usually is in between 2.2 and 5 and preferably between 2.5 and 4.5 mol/mol. For completeness' sake, it is noted that the synthesis zone will usually operate on the basis of both an external feed of the starting materials, ammonia and carbon dioxide, and recycled starting materials, generally comprising recycled ammonia and carbon dioxide in a free form as well as in the form of ammonium carbamate and/or biuret. The gross N/C ratio, which is a term having a customary meaning in the art, refers to a hypothetical mixture in which all starting materials are converted into free ammonia and carbon dioxide.

The synthesis zone can comprise a single reactor or a plurality of reactors, arranged in parallel or in series. In addition to one or more reactors, the synthesis section comprises a stripper, a condenser and a scrubber, all operating at substantially the same pressure. The synthesis zone is generally referred to as a High Pressure (HP) section.

In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, high pressure (HP) steam is added to heat the solution via indirect heat exchange. The urea solution leaves the heat exchanger at the bottom part, while the vapor phase leaves the stripper at the top part. The vapor leaving said stripper contains ammonia, carbon dioxide and a small amount of water. Said vapor is condensed in a falling film type heat exchanger or a submerged type of condenser that can be a horizontal type or a vertical type. A horizontal type submerged heat exchanger is described in the aforementioned Ullmann's Encyclopedia of Industrial Chemistry, Vol. A27, 1996, pp 333-350.

After the stripping treatment, the pressure of the stripped urea solution is reduced in a urea recovery section. In the recovery section the non-converted ammonia and carbon dioxide in the urea solution are separated from the urea and water solution. A recovery section comprises usually a heater, a liquid/gas separation section and a condenser. The urea solution entering a recovery section is heated to vaporize the volatile components ammonia and carbon dioxide as well as water from that solution. The heating agent used in the heater is usually steam. The ammonium carbamate aqueous solution formed in a low pressure carbamate condenser in the recovery section, operated at a lower pressure than the pressure in the synthesis section, is preferably returned to the urea synthesis section operating at synthesis pressure. The recovery section is generally a single section or can be a plurality of recovery sections arranged in parallel or in series. The recovery section comprises a heater, a liquid/gas separator and a condenser. The pressure in this recovery section is generally between 200 to 600 kPa. This section is generally referred to as a low pressure (LP) recovery section (or recirculation section, the terms "recovery section" and "recirculation section" in this description are used interchangeably). In the heater of the recovery section the bulk of ammonia and carbon dioxide is separated from the urea and water phase by heating the urea solution. Usually low pressure (LP) steam is used as heating agent. The urea and water phase contains a small amount of dissolved ammonia and carbon dioxide that leaves the recovery section and is sent to a downstream urea processing section where the urea solution is concentrated by evaporating the water from said solution. This section is typically referred to as the evaporation section and it is typically comprised of one or two evaporators, whose vapors are condensed downstream and recycled back to the process.

In some embodiments, in addition to the HP synthesis section and the LP recovery section, a medium pressure (MP) treatment section is present. E.g., WO 02/090323 discloses a urea process and plant of the carbon dioxide stripping type, wherein a MP treatment section is present parallel with the HP stripping section. A similar disclosure is found in EP 2 086 928.

Processes also exist in which a MP treatment section is present in series, downstream of the urea synthesis section. In this respect reference can be made to, e.g., GB 1 542 371, and other disclosures of the Snamprogetti Ammonia and Self-Stripping processes.

In the development of the field of urea production processes and plants, it is permanently sought to improve one or more of various output parameters. Thus, it is desired to further improve yield. It is also desired to improve the efficiency of recirculation of residual reactants. Further, it is desired to reduce, or at least further optimize, one or more of the energy consumption, the operational expenses (OPEX), and the capital expenses (CAPEX).

The inventors have, inter alia, identified a general challenge in respect of the energy used in a urea plant. In the plants to date, a large amount of internal energy is wasted in the expansion of the process stream due to the inevitable pressure drop between the HP synthesis section and the LP (or MP and LP) downstream sections. It would be desired to provide a urea process and plant allowing making use of at least part of said otherwise wasted internal energy. In this respect it is noted that in thermodynamics, the internal energy of a system is energy contained within the system, excluding the kinetic energy of motion of the system as a whole and the potential energy of the system as a whole due to external force fields. It keeps account of the gains and losses of energy of the system that are due to changes in its internal state. The invention refers to the use of internal energy as work (i.e., not as heat).

Background art includes EP 1491526. Therein, in a urea production process, an expansion step is provided, in a turbine, of the reaction mixture coming from high pressure synthesis. Kinetic energy produced by the turbine is put to use elsewhere in the process.

Another background reference is WO 2013/104638. This relates to the use of a passivating agent in an otherwise conventional thermal stripping process for producing urea. As is typical for thermal (self) stripping processes, the stripper is operated at a pressure slightly below that of the urea synthesis reactor.

SUMMARY OF THE INVENTION

In order to better address one or more of the aforementioned desires, the invention provides, in one aspect, a plant for the production of urea comprising a synthesis section configured to be operated under a high pressure between 12 and 40 MPa and a recovery section configured to be operated under a pressure below 7 MPa, said synthesis section comprising, connected so as to be capable of forming a urea synthesis loop, a urea reactor, a stripper, a condenser and, optionally, a scrubber, wherein the synthesis section is configured so as to allow the reactor to be operated under a pressure substantially higher than the pressure of the stripper and the condenser, and wherein the synthesis section comprises a compression unit positioned downstream of the condenser and upstream of the reactor, said compression unit being configured so as to increase the pressure of a fluid, such as a liquid condensate, obtained from the condenser to substantially the same pressure under which the reactor is operated, whereby said compression unit is configured to utilize mechanical energy recovered from a decompression unit positioned downstream of the stripper and upstream of the recovery section.

In another aspect, the invention presents a method of modifying a pre-existing urea stripping plant so as to provide a modified plant, said pre-existing plant comprising a synthesis section adapted to operate under a high pressure between 12 and 40 MPa and a recovery section adapted to operate under a pressure below 7 MPa, said synthesis section comprising, connected so as to be capable of forming a urea synthesis loop, a urea reactor, a stripper, a condenser and optionally a scrubber, wherein the modifying of the pre-existing plant comprises adding a compression unit in a position downstream of the condenser and upstream of the reactor, wherein the synthesis section is configured so as to allow the reactor to be operated under a pressure substantially higher than the pressure of the stripper and the condenser, said compression unit being adapted so as to increase the pressure of a fluid, such as a liquid condensate, obtained from the condenser to substantially the same pressure under which the reactor is operated, whereby said compression unit is configured to utilize mechanical energy recovered from decompression of liquid downstream of the stripper and upstream of the recovery section.

In a further aspect, the invention also presents a method of modifying a pre-existing urea recycle plant so as to provide a modified plant, said pre-existing plant comprising, placed in series, a HP reactor adapted to be operated at a high pressure of 16 to 40 MPa so as to obtain a urea synthesis solution, a MP recirculation section adapted to be operated at a medium pressure of 1 to 5 MPa, and a LP recirculation section adapted to be operated at a low pressure of 0.1 to 1 MPa, said recirculation sections adapted to decompose ammonium carbamate and to recirculate a liquid condensate comprising non-reacted carbon dioxide and ammonia and liquid components comprising ammonium carbamate, back to the reactor, the method comprising:

adding a HP stripper downstream of the reactor and upstream of the MP recirculation section, said stripper being adapted so as to direct liquid obtained therefrom to either or both of the MP and LP recirculation sections;

adding a HP condenser, whereby the HP condenser and the HP stripper are mutually arranged such as to subject gas obtained from the HP stripper to condensation in said HP condenser so as to form a liquid condensate and remaining vapors;

arranging said HP condenser in connection with a compression unit positioned downstream of the condenser and upstream of the reactor wherein said compression unit is configured so as to increase the pressure of a fluid, such as a liquid condensate, obtained from the condenser to substantially the same pressure under which the reactor is operated, whereby said compression unit is configured to utilize mechanical energy recovered from decompression of liquid downstream of the stripper and upstream of the recovery section.

In yet another aspect, the invention is a process for the preparation of urea in a urea production plant, said plant comprising a synthesis section operating under a high pressure between 12 and 40 MPa and a recovery section operating under a pressure below 7 MPa, said synthesis section comprising a urea reactor, a stripper, a condenser and optionally a scrubber, the process comprising the steps of:

a) reacting ammonia and $CO_2$ under urea forming conditions in the urea reactor to obtain a urea synthesis solution;

b) stripping the urea synthesis solution in the stripper to form a stripped urea solution and a stripper vapor comprising mostly ammonia and $CO_2$;

c) condensing the stripper vapor obtained in b) in the condenser to form an ammonium carbamate solution;

d) recirculating said ammonium carbamate solution to the reactor;

e) recovering ammonium carbamate from the stripped urea solution to ammonium carbamate recovery in the recovery section;

f) recycling the recovery vapor to the urea synthesis section;

the process further comprising operating the urea reactor under a pressure at least 2 MPa higher than the pressure of the stripper and the condenser, and increasing the pressure of the ammonium carbamate solution upon recirculation to the reactor, wherein energy utilized in increasing said pressure comprises mechanical energy recovered from a decompression unit positioned downstream of the stripper and upstream of the recovery section.

DETAILED DESCRIPTION OF THE INVENTION

Figure 1:
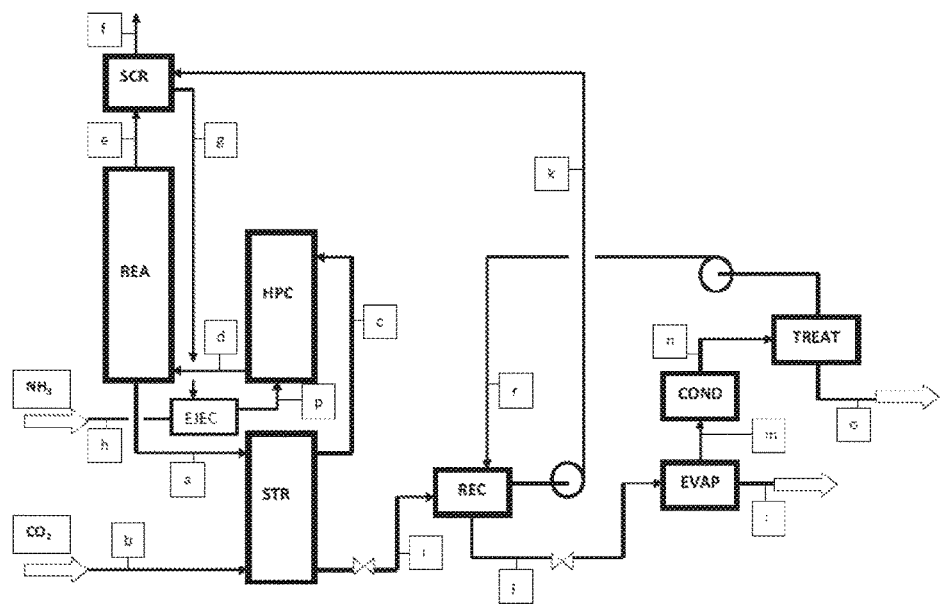
FIG. 1 shows a process scheme for a urea stripping process according to prior art using carbon dioxide as a stripping agent.

The invention is based, in a general sense, on the judicious insight to combine the recovery of mechanical energy from a urea plant comprising a stripper in its high-pressure synthesis section, with creating in said urea plant a pressure in the urea synthesis reactor that is higher than the pressure in the stripper.

Thereby it is realized to modify the urea process and plant so as to build in a useful additional compression step, respectively installing a corresponding compression device therefor. By virtue of the foregoing insights, the inventors have also realized to provide a general improvement in urea synthesis, by separating the pressure level in the urea reactor from that in the remaining parts of the urea synthesis section.

Where in this description, the component parts of a urea plant are discussed, including units, zones, and sections of such a plant, the skilled person will understand how to conduct a urea production process therewith. I.e., also if not explicitly stated, the skilled person will understand the mutual arrangement of such parts. For instance, the skilled person will understand the following: A urea production plant generally comprises fluid connections and lines for process streams (urea production streams), generally including a recirculation circuit. This serves to synthesize and obtain urea, and to make optimal use of reactants by recirculation of unreacted ammonia and carbon dioxide. A urea plant generally also comprises utility connections and lines, generally including a steam circuit. This serves to provide heat where needed in the plant, and to make optimal use of available energy by circulating steam obtained in one part of the plant to another part where heat exchange from such steam can be benefited from. Thereby, also if not explicitly indicated, the person skilled in urea production will normally be able to tell which are liquid streams and which are gas streams, and through which ducts, pipes, or flow lines these are transported and/or recirculated in the plant.

Where, in this description, it is spoken of "fluid communication", this refers to any connection between a first part or section of a plant and a second part or section of a plant via which fluids, i.e., gases, liquids, or supercritical fluids, and more particularly liquids, can flow from the first part of the plant to the second part of the plant. Such fluid communication is typically provided by piping systems, hoses, or other devices well-known to the skilled person for the transportation of fluids.

Where in this description it is spoken of "gas flow lines" this refers to any connection between a first part or section of a plant and a second part or section of a plant via which gas or vapors, notably aqueous vapors, can flow from the first part of the plant to the second part of the plant. Such gas flow lines typically comprise piping systems, or other devices well-known to the skilled person for the transportation of gases, if needed under above or below (vacuum) atmospheric pressures.

Bi-pressurized Synthesis Section

In one aspect, the present invention provides, in marked deviation from a conventional urea production plant, a bi-pressurized synthesis section. This is particularly non-conventional in a urea plant of the carbon dioxide stripping type. Accordingly, the synthesis section is configured so as to allow the reactor to be operated under a pressure substantially higher than the pressure of the stripper. It will be understood that such configuration of the synthesis section generally takes into account the presence of one or more pressure regulators. This refers to, e.g., a decompression unit, such as a pressure control valve, to reduce the pressure between the reactor and the stripper.

Hereby the HP stripper and the HP condenser are operated at substantially the same pressure. The reactor is operated at a substantially higher pressure than the stripper and the condenser. Generally, the pressure difference will be such that the pressure of the reactor is at least 5 bar (0.5 MPa) higher than the pressure of the stripper. The advantage of a higher pressure is that a higher temperature can be achieved in the reactor so the urea yield will increase. Preferably, said pressure difference is at least 1 MPa bar, such as at least 2 MPa, e.g. up to 10 MPa. More preferably, the pressure difference ranges from 2 MPa to 5 MPa, such as from 3 MPa to 4 MPa. In an interesting embodiment, the stripper and the condenser are operated under a pressure of from 13 to 15 MPa, and the reactor is operated under a pressure of 16 to 21 MPa. E.g., the stripper and the condenser are operated at 14-14.5 MPa in a temperature range of 170-190° C., and the reactor at 17-20 MPa in a temperature range of 180-200° C.

The skilled person will have no difficulty to set the desired pressures for the various units comprised in the synthesis section, i.e., at least the reactor, the stripper, and the condenser. These units all constitute known equipment, normally designed to be operated under high pressure, and normally adapted so as to set the operational pressure.

In order to operate the synthesis section in accordance with the invention, at a pressure exceeding that of the HP condenser, it will be understood that measures are to be taken to increase the pressure of fluid leaving the HP condenser up to the pressure of the reactor. This can be realized by suitably positioning a compression device, i.e., downstream of the HP condenser and upstream of the reactor, whereby the terms "downstream" and "upstream" refer to the flow of fluid, such as liquid ammonium carbamate condensate, from a fluid outlet of the HP condenser, such as a liquid outlet, to a fluid inlet of the reactor, such as a liquid inlet. Suitable compression devices are known to the skilled person, and include, e.g., pumps and ejectors, as well as compressors in the event that the fluid flowing from the HP condenser to the reactor is a gas. It will be understood that also a combination of liquid and gas is possible. I.e. a compressor for gas and a pump for liquid. The liquid and the gas may be separated before the pressure is increased.

The presence of a compression device between the HP condenser and the reactor comes with an additional advantage. By virtue of the pressurization of the liquid flow into the reactor, the HP condenser and the reactor can be positioned vis-à-vis each other without taking into account gravity flow (which is a customary flow driver in urea plants) or taking it into account only partially. As a result, the reactor can be placed on a relatively low level, such as on the ground. This is a general advantage in terms of construction and accessibility for maintenance. Moreover, as a result, the reactor can be well placed in vertical position, so as to occupy a much smaller footprint than in the event of a—frequently occurring—horizontal placement.

The aforementioned presence of a compression device enables operating the reactor at a pressure and temperature optimized for urea synthesis, and at the same time conducting stripping (and subsequent condensation) at a pressure and temperature optimized for stripping efficiency.

Accordingly, as compared to the conventional situation wherein the reactor, the HP stripper, and the HP condenser are operated at substantially the same pressure, the reactor can be operated so as to provide a higher yield of urea. Or, similarly, with the same yield, a smaller reactor can be employed. E.g., this can be of advantage in building a grass-roots plant (i.e. a new plant). Therein the reactor can be smaller than in conventional plants. This presents advantages in terms of capital investments (since lower amounts of expensive, highly corrosion-resistant materials are needed for the construction of the reactor). It also presents advantages in terms of operational expenses, as the energy requirements for a smaller reactor, as well as the maintenance expenses, will generally be reduced as well.

The plant of the invention can be constructed using regular components known in the art. This refers, e.g. to reactors and stripper components made of highly corrosive-resistant duplex steel, e.g. as known under the name of Safurex®. This also refers to known types of equipment, such as heat exchangers, for example shell and tube heat exchangers, submerged (pool) condensers, and the like. An advantage of employing pool condensation in the synthesis section, is that a considerable conversion into urea already takes place in the condenser. Since, as a result of the invention, the reactor operates at a higher efficiency, the invention also results in a capacity increase. Such a capacity increase may refer to designing a new plant having a higher capacity. Preferably it refers to modifying a pre-existing plant so as to increase its capacity.

Thus, the higher yield of urea obtained in the reactor, also presents an advantage in a method of modernizing a pre-existing urea plant. In such a method, e.g. a revamping method, it is frequently desired to increase the capacity of the pre-existing plant. The invention makes it possible, with the same size of reactor, to obtain a higher urea yield, as a result of employing a higher overall pressure in the synthesis section. Accordingly, in an interesting embodiment the pressure of the HP stripper and the HP condenser as present in a pre-existing plant will remain unchanged, and the pressure in the reactor will be increased. It is noted that, as a result of the higher conversion yield in the reactor, the stripping requirement may be correspondingly lower. It will be understood that, in order to retain the necessary gas input to the reactor, also the gas phase from the HP condenser to the reactor will be suitably compressed. In the alternative, carbon dioxide is added. I.e., since the higher yield is based on conversion, lower amounts of unreacted ammonia and carbon dioxide will remain. Thus, the method of the invention advantageously does not require modifications of the other units in the synthesis section, viz. the HP stripper and the HP condenser. It will be understood that a higher yield may require expanding the capacity of downstream sections of the urea production plant. Expanding the capacity of a section may involve, e.g., expanding the size of the section, increasing the throughput efficiency of a section, increasing the conversion efficiency of a section, or a combination of any of these and/or other measures generally available to the skilled person. This will not present any difficulty for the skilled person. Also, expanding the (MP and/or LP) downstream sections (which are operated at pressures far below that of the synthesis section) is generally less costly than expanding HP units.

A further advantage of the invention, specifically for CO2 stripping plants, is related to the higher conversion yield, and the, relatively, reduced stripping requirement associated therewith. In conventional carbon dioxide stripping plants, wherein normally the striper and the reactor are operated under the same pressure, the carbon dioxide feed is regularly fed to the stripper, as a stripping agent. In the present case, however, the optimum for the amount of carbon dioxide stripping gas allows carbon dioxide to be directly fed to the reactor. This, in turn, has the advantage that, since condensation of the carbon dioxide feed to a liquid phase provides heat, additional heat is automatically provided by the carbon dioxide feed, and thus without requiring an additional source of heat energy. The direct $CO_2$ addition also gives a method for controlling the N/C ratio in the reactor, and in this regard, a direct $NH_3$ feed to the vertical reactor could be added too. Direct $CO_2$ addition to the low pressure recovery section, e.g. to the low pressure carbamate condenser is also conceivable.

Energy from Pressure Drop

As indicated above, a particular aspect of the present invention, in a generally preferred embodiment, involves employing energy that becomes available from expansion of a process stream in a urea production plant. This occurs as a result of a pressure drop between the HP synthesis section, and a downstream section operating under a lower pressure (such as an LP or MP recovery section). To this end, in brief, a compression unit is present that is configured to utilize mechanical energy recovered from an energy losing source. The recovered mechanical energy thereby is in fact internal energy that is recovered and converted into mechanical energy.

In accordance with this aspect of the invention, the aforementioned additional compression unit downstream of the HP condenser and upstream of the reactor, can be operated without substantial additional energy input. This can be accomplished by a compression unit that is capable of converting a pressure difference into mechanical energy (work). A typical example hereof involves the IsoBoost system of Energy Recovery™. This is a hydraulic system that recovers pressure energy by means of a liquid-to-liquid turbocharger. The turbocharger recovers internal energy, in the form of work, from the pressure reduction of a high-pressure fluid and transfers it to a low-pressure fluid to reduce, or ideally eliminate, the energy required for pumping.

Other systems suitable for the conversion of liquid depressurization energy into mechanical recompression of another liquid, are available. E.g. from Calder AG based in Switzerland; ("Energy Recovery Turbine, ERT, Application"). From Fluid Equipment Development Company (FEDCO) based in Monroe, Mich. ("Hydraulic Pressure Boosters (HPBs)"). From Pump Engineering Incorporated (PEI) based in Monroe, Mich.

Thus, in the plants designed or modified according to the invention, the compression unit is configured to obtain compression energy from one or more events in the urea production process (i.e., at one or more points in the urea production plant), at which a loss of energy occurs, such as decompression of a high energy stream. The decompression unit and the compression unit together are designed so as to be capable of converting a pressure difference into work. E.g., in a preferred embodiment, the decompression unit and the compression unit share a common rotating axis configured to be driven by liquid depressurization energy obtained from the decompression unit. Thereby the decompression unit and the compression unit preferably are integrated in a single device.

In the plants as designed, used, or modified in accordance with the invention, the available pressure difference is provided by the difference under which the HP stripper and the lower pressure (LP or MP) downstream sections are operated. Accordingly, in these embodiments the compression unit is configured to utilize mechanical energy recovered from a decompression unit positioned downstream of the stripper and upstream of the recovery section. Thereby the decompression unit is in fluid communication with a liquid outlet from the stripper comprised in the synthesis section.

Hereinbefore, the invention has been discussed primarily in connection with a urea plant. Thereby the invention is applicable both to the construction of new urea plants ("grass root" plants) as well as in revamping existing urea plants. Interestingly, the invention provides not only a possibility for modifying a pre-existing urea stripping plant, but also a method of modifying a urea plant of the conventional recycle type (sometimes also referred to as a "total recycle plant") into a stripping plant Thus, the invention includes a method of modifying a pre-existing urea stripping plant. Such a plant normally comprises a synthesis section adapted to operate under a high pressure between 12 and 40 MPa, and a recovery section adapted to operate under a pressure below 7 MPa. The high pressure (HP) synthesis section preferably is operated at 12 MPa to 25 MPa, and more preferably from 12 MPa to 20 MPa, such as 14 MPa to 18 MPa. Preferably stripping takes place at 12 to 16 MPa. Generally, the synthesis section comprises, connected so as to be capable of forming a urea synthesis loop, a urea reactor, a stripper, a condenser and optionally a scrubber. In some embodiments, as the skilled person will be aware, a stripping plant also comprises a medium pressure (MP) treatment section. Such a section can be placed, e.g., in series downstream of the synthesis section, but it may also be downstream of the reactor, in parallel with the HP stripper and condenser. Reference is made to, e.g., WO 02/090323 or EP 2 086 928.

The method of modifying a pre-existing urea stripping plant comprises adding a compression unit in a position downstream of the condenser and upstream of the reactor. Further, the method comprises, to the extent necessary, adapting the reactor so as to be operated under a pressure substantially higher than the pressure of the stripper and the condenser. Normally, the reactor and associated equipment of a urea stripping plant will as such be capable of being operated under a higher pressure.

In accordance with this aspect of invention, the added compression unit is adapted so as to increase the pressure of a fluid, such as a liquid condensate, obtained from the condenser to substantially the pressure under which the reactor is operated.

The pressures under which the reactor is operated, as well as the pressures under which the stripper and the condenser are operated, are as discussed above.

As said, the invention also presents a method of modifying a pre-existing urea total-recycle plant. Such a pre-existing plant, which is a type of plant that does not comprise a stripper and a condenser, will normally comprise, placed in series, a HP reactor adapted to be operated at a high pressure of 15 to 40 MPa so as to obtain a urea synthesis solution, a MP recirculation section adapted to be operated at a medium pressure of 1 to 7 MPa, and/or an LP recirculation section adapted to be operated at a low pressure of 0.1 to 1 MPa. It will be understood that said recirculation section or sections are adapted to decompose ammonium carbamate and to recirculate condensed gaseous components comprising non-reacted carbon dioxide and ammonia, and liquid components comprising ammonium carbamate, back to the reactor. The HP reactor more typically is configured to be operated at a pressure of from 16 MPa to 35 MPa, preferably of from 20 MPa to 30 MPa. The modification method of the invention comprises the following steps, referring to the addition of components conventionally present in a urea stripping plant:

adding a HP stripper downstream of the reactor and upstream of the LP (or MP) recirculation section;

adding a HP condenser downstream of a gas outlet of the HP stripper.

In the modified plant, the synthesis section resulting from the modification is configured so as to allow the reactor to be operated under a pressure substantially higher than the pressure of the stripper and the condenser. As mentioned above, this will generally imply the presence of a pressure regulating device which reduces the pressure between the reactor and the stripper. Advantageously, part of the liquid leaving the reactor is thereby subjected to flash evaporation. Thereby the flash evaporated liquid will move in the stripper as a gas, generally upwards in a gas stream leaving the stripper, instead of flowing as a liquid, typically downwards through a stripper tube.

The added stripper is adapted so as to direct liquid obtained therefrom to either or both of the MP and LP recirculation sections. The added condenser and the added stripper are arranged so as to subject gas obtained from the stripper to condensation in said condenser so as to form a liquid condensate and remaining vapors.

The method further comprises steps of arranging, if necessary re-arranging, how certain components are connected:

optionally arranging said HP condenser in connection with a scrubber, which will typically send liquid to an ejector designed to feed the HP condenser. This can refer to an added HP scrubber, but it can also be an added or existing MP or LP scrubber, which has the aforementioned advantage that the additional HP piece of equipment of a HP scrubber can be dispensed with. The scrubber is adapted so as to subject the above-mentioned remaining vapors to scrubbing and to recirculate resulting absorbed/condensed gases in the form of ammonium carbamate back to the synthesis section, particularly to the reactor or to a pool condenser;

arranging the above-mentioned HP condenser in connection with a compression unit positioned between the liquid outlet of the condenser and the liquid inlet of the reactor, and in fluid communication therewith. This compression unit is adapted so as to increase the pressure of fluid, such as the liquid condensate, to the pressure under which the reactor is operated.

The aforementioned compression unit can be a compression unit as normally present in this type of (conventional recycle) urea production plants. In a preferred embodiment, the compression unit is chosen such as to be capable of converting a pressure difference into mechanical energy. I.e., in this embodiment the modification method of the invention comprises adding a compression unit to the pre-existing plant. Thereby said compression unit advantageously is in the form of an energy recovery system as referred to above. The fluid by the expansion of which, by conversion, mechanical energy is generated, preferably is a liquid in view of the availability of systems for the recovery of internal energy from such expansion, and converting same in to mechanical energy. However, it can also be a gas. The fluid of which the pressure is increased can be a liquid, a gas, or (as will frequently occur) both. In the latter event, it is conceivable that the pressure of both the liquid and the gas is increased. It is preferred, taking into account the availability of systems for the recovery of mechanical energy, that particularly the pressure of the liquid is increased.

MP Treatment

The presence (or, as appropriate, the addition) of a MP treatment section presents a generally interesting embodiment of the various aspects of the invention. I.e., this is applicable to the urea production plants of the invention, as well as to the aforementioned methods of modifying pre-existing plants.

In this embodiment, the presence of the above-discussed bi-pressurized synthesis section, is suitably combined with the presence of a medium pressure treatment section. It has been unexpectedly found that the pressure reduction from the HP stripper to a MP (medium pressure) treatment section is sufficient to drive a compression unit, such as the aforementioned IsoBoost system, or other compression units that are capable of converting a pressure difference into mechanical energy.

The MP treatment section possibly comprises a MP decomposer, either as a single apparatus, or in the form of a MP dissociator coupled, in series, to a MP stripper. The MP section will generally also comprise a MP condenser, for condensing gas coming from the MP dissociator and/or stripper.

It will be understood that a dissociator and a stripper can comprise two different units, typically placed in series, or can be one and the same unit. Generally, in a stripper also dissociation will take place. This may result from heat, but this also applies in the event that a stripping agent is used. The stripping agent (typically carbon dioxide or ammonia) will remove ammonia and/or carbon dioxide as gaseous components from the ammonium carbamate comprising liquid subjected to stripping. As a result of the removal of said gaseous components, the equilibrium in the liquid will shift to further dissociation of ammonium carbamate into its components. Whilst, accordingly, a stripper is necessarily a dissociator, a dissociator is not necessarily a stripper. A separate dissociator, in the field of urea production, will normally serve to subject ammonium carbamate to dissociation energy, typically in the form of heat, as a result of which ammonium carbamate breaks up into ammonia and carbon dioxide. Both a stripper and a dissociator generally are heat exchangers in which heat is exchanged indirectly between steam and the process stream that is subject to the action of the stripper or dissociator.

In the foregoing embodiment, it is also possible, for further removal of ammonia and carbon dioxide, to absorb the uncondensed gas stream leaving the medium-pressure condenser in a medium-pressure scrubber. A preferred MP treatment section comprises a MP adiabatic flash separator.

An advantage of the configuration of the invention, particularly in the event of providing MP treatment, is that a HP scrubber can be dispensed with. This is a general advantage in view of the expensive nature of HP scrubbing devices. Moreover, it adds a particular advantage for methods of modifying existing urea plants of the conventional total recycle type. In the method of the invention the necessary HP and energy recovery compression equipment is installed. The technical possibility to avoid also installing a HP scrubber then adds a significant economic advantage as compared to existing processes of modifying a conventional plant into a stripping plant. A further advantage is related to safety. A HP scrubber contains a significant amount of ammonia which is capable of forming flammable mixtures, especially in the event of $H_2$ becoming mixed with $NH_3$. Particularly the scrubber off-gas may be prone to the generation of such mixtures, as the $NH_3$ and $CO_2$ contents decrease in the gas phase while the $H_2$ is a highly flammable non-condensable whose volume fraction becomes larger over the overhead operations. When avoiding the HP scrubber, this risk is lower since the gas stream that would otherwise have been sent to the HP scrubber will necessarily decompressed, i.e. become expanded or in other words, its volume would increase. As a result thereof, the $H_2$ volume fraction decreases, and so does flammability.

In a further aspect, the invention also provides a process for the preparation of urea in a urea production plant. Preferably, the plant will be a plant (either a new plant or a modified pre-existing plant) in accordance with the descriptions thereof given hereinabove.

In the process of the invention, said plant comprises a synthesis section operating under a high pressure between 12 and 40 MPa and a recovery section operating under a pressure below 1 MPa. The synthesis section comprises urea reactor, a stripper, a condenser and optionally a scrubber. According to the invention, the process for the preparation of urea comprises the steps of:

a) reacting ammonia and $CO_2$ under urea forming conditions in the urea reactor to obtain a urea synthesis solution;

b) stripping the urea synthesis solution in the stripper to form a stripped urea solution and a stripper vapor comprising ammonia, $CO_2$ and a small amount of water (typically of the order of 42% wt (55-40) NH3, 53% wt. CO2 (40-55) and 5% wt (2-10) H20);

c) condensing the stripper vapor obtained in b) in the condenser to form an ammonium carbamate solution;

d) recirculating said ammonium carbamate solution to the reactor;

e) subjecting the stripped urea solution to ammonia and carbon dioxide recovery in the recovery section to obtain a urea product solution and a recovery vapor comprising ammonia and carbon dioxide;

f) recycling a condensate obtained from the recovery vapor to the urea synthesis section.

A preferred type of condensation is pool condensation, e.g. in a submerged condenser. A submerged condenser is typically a horizontal or a vertical submerged condenser. The term "pool condenser" can also be used. In a preferred embodiment, the submerged condenser is a horizontal pool condenser. It is noted, as the skilled person will be aware, that pool condensation goes together with a significant amount of conversion of ammonium carbamate into urea. In many urea plants, and as also preferred in the present invention, the first contact of the reactants $NH_3$ and $CO_2$ occurs in the (HP) condenser rather than in the reactor.

The process of the invention thereby comprises reacting ammonia and carbon dioxide in the urea reactor under a higher pressure than whereby the stripper and the condenser are operated, preferably at least 0.5 MPa higher, such as of from 1 MPa up to 10 MPa, such as in range of from 2 MPa to 5 MPa higher. Accordingly, the process of the invention also comprises a step of increasing the pressure of the ammonium carbamate solution upon recirculation to the reactor and decompression of the synthesis solution obtained from the reactor when such is sent to the stripper.

It is noted that, as a result of the present invention, the inventors also provide a urea plant (and corresponding modifications of existing urea plants) comprising a synthesis section configured to be operated under a high pressure between 12 and 40 MPa (preferably 12-25 MPa, more preferably 12-20 MPa) and a recovery section configured to be operated under a pressure below 7 MPa, said synthesis section comprising, connected so as to be capable of forming a urea synthesis loop, a urea reactor, a stripper, a condenser and, optionally, a scrubber, wherein the synthesis section is configured so as to allow the reactor to be operated under a pressure at least 0.5 MPa higher than the pressure of the stripper and the condenser, such as up to 10 MPa, and preferably of from 2 MPa to 5 MPa, and wherein the synthesis section comprises a compression unit positioned downstream of the condenser and upstream of the reactor, said compression unit being configured so as to increase the pressure of fluid, such as liquid condensate obtained from the condenser to substantially the same pressure under which the reactor is operated. This plant will have the earlier indicated benefits of a bi-pressurized synthesis section. It will be understood that this plant can be provided in all of the aforementioned embodiments, preferably including an energy recovery system in accordance with the invention as described hereinbefore.

The invention will hereinafter be further illustrated with reference to the following, non-limiting figures.

FIG. 1 represents a known urea stripping process using carbon dioxide as a stripping agent.

The high pressure synthesis section comprises a reactor (REA), a stripper (STR), a condenser (HPC) and a scrubber (SCR) that comprises a scrubber bed and/or a heat exchanger. The synthesis section is typically operated at a pressure in between 13 and 16 MPa and the equipment parts in the synthesis section are in fluid communication. Preferably, the fluid communication is based on a flow due to communicating vessels, i.e., due to hydrostatic pressure and preferably without pumps. The synthesis process loop generally involves gravity flows.

In the synthesis section the urea solution leaving the urea reactor (REA) is fed (a) to a stripper (STR) in which a large amount of non-converted ammonia and carbon dioxide is separated from the aqueous urea solution. The stripper is a shell and tube heat exchanger in which the urea solution is fed to the top part via line (a) at the tube side and a carbon dioxide feed is added to the bottom part of the stripper via line (b) at the tube side too. The carbon dioxide may but not necessarily contain inert and may comprise air for protecting the fabrication materials of the equipment and lines in the synthesis section against excessive corrosion. The urea solution from the reactor (REA) supplied to the stripper (STR) via line (a) is counter currently contacted with the supplied carbon dioxide. By this the partial pressure of ammonia and $CO_2$ in the urea solution are decreased, which causes the non-converted ammonium carbamate to decompose. As a heating agent, steam at a pressure of 1.5 to 2.5 MPa is supplied for the purpose of indirect heat exchange, typically to the shell side of said stripper (STR) in order to provide the heat of dissociation of the ammonium carbamate and to obtain a urea concentration in the urea solution leaving that stripper of approximately 53 to 56% by weight. The vapor leaving the stripper (STR) via line (c) contains ammonia, carbon dioxide, inerts and a small amount of water, and is supplied to a condenser (HPC). Ammonia is supplied to that high pressure condenser (HPC) as well, via line (p). In this condenser the ammonia and carbon dioxide are condensed into an ammonium carbamate solution. If the high pressure condenser (HPC) is of a submerged type, residence time of the liquid phase is created, which causes the endothermic urea reaction to occur. The released condensation heat is exchanged indirectly with process condensate and used to form low pressure (LP) steam that is typically used as a heating agent elsewhere in the process, e.g. as heating agent in the evaporation section and/or as a driving force for ejectors. The thus formed ammonium carbamate solution together with non-condensed inert vapor leaving the condenser (HPC) is sent via line (d) to the reactor (REA), where the endothermic urea reaction approaches the equilibrium. It is noted that line (d), in practice, will usually comprise two different lines, viz. one configured to carry gas and the other configured to carry liquids.

In the top of the reactor (REA) the solution is separated from the non-condensed vapor that comprises next to ammonia and carbon dioxide also inerts. The urea solution leaving the reactor (REA) is typically controlled at an ammonia to carbon dioxide molar ratio in the range of 2.8 to 3.2 mol/mol and the water to carbon dioxide molar ratio in the urea solution leaving the reactor (REA) is typically in the range of 0.45 to 0.7 mol/mol and usually in the range 0.5 to 0.65 mol/mol. The non-condensed inert vapor leaving the reactor (REA) is sent to the scrubber (SCR) via line (e). In the scrubber (SCR) the non-condensed ammonia and carbon dioxide is separated from the inert vapor by feeding the ammonium carbamate, formed in the recovery section as absorbent via line (k). The inert vapor via line (f) is sent into the atmosphere directly or is treated in an absorber before releasing it into the atmosphere. The formed ammonium carbamate solution in the scrubber (SCR) is returned to the condenser (HPC) via line (g). In most cases the pressure of the formed ammonium carbamate solution in the scrubber (SCR) is increased by an ammonia ejector (EJEC) before it enters the condenser (HPC) via line (p). As a driving force for this ejector (EJEC) the liquid ammonia feedstock is used that enters said ejector via line (h).

The urea solution leaving the urea stripper (STR) via line (i) comprises typically in between 9 and 14% by weight of non-converted carbon dioxide and is expanded, typically through an expansion valve, and sent directly to a recovery section (REC). The operating pressure in the recovery section is usually 0.2 to 0.6 MPa. The recovery section comprises usually a decomposer (e.g. a rectifying column) and a condensation section. The decomposer is usually a shell and tube heat exchanger. In the decomposer the ammonium carbamate left in the urea solution is fed to the tube side of the shell and tube heat exchanger and decomposed into ammonia and carbon dioxide vapor by adding steam to the shell side. The urea solution leaves said decomposer at a temperature of 120-145° C. and preferably at a temperature of 130 to 140° C. after which the pressure of said urea solution is decreased causing a further purification of the urea solution by flashing.

The released vapor from the decomposer comprising ammonia, carbon dioxide and water is condensed in a low pressure carbamate condenser (LPCC) comprised in the recovery section (REC), thereby forming an ammonium carbamate solution that is recycled to the synthesis section. Preferably, but not necessarily, the ammonium carbamate is pumped to the scrubber (SCR) in the synthesis section.

The urea solution leaving the recovery section (REC) arrives via line (j) in the evaporation section (EVAP). In this evaporation section (EVAP) the urea solution is concentrated to the desired urea concentration that is determined by the finishing section (not shown). Usually the concentration of the urea solution takes place at sub-atmospheric pressure and dependent on the required concentration one or a plurality of evaporators are used. The concentrated urea solution leaves the evaporation section via line (l). The released vapor leaving the evaporators via line (m) comprising water, ammonia and carbon dioxide is condensed to form process condensate. Since the operating pressure in the evaporator is sub-atmospheric, small amounts of urea are entrained and leave the evaporators via the vapor phase. This urea is traced back in the formed process condensate leaving the condensation section (COND) via line (n). Said formed process condensate is thereafter totally or partially being used as absorbent in the absorbers of the plant to purify inert vapor, subjected to a process condensate treatment section (TREAT). The process condensate treatment section comprises a first desorber, a hydrolyser column followed by a next second desorber (not shown). In the first desorber the bulk of ammonia and carbon dioxide is stripped from the water solution. The stripped condensate is subjected to a heated liquid filled column (hydrolyser) in which the urea, occurring in said condensate, is decomposed into ammonia and carbon dioxide. The effluent leaving this hydrolyser comprising water, ammonia and carbon dioxide is subjected to the next second desorber in which the residual ammonia and carbon dioxide is stripped from the condensate. Usually steam is used as stripping agent in this second desorber. The purified process condensate leaves the treatment section (TREAT) via line (o). The hot off-gas leaving the second desorber comprising ammonia and carbon dioxide is usually used as stripping agent for the said first desorber. The off-gases leaving the first desorber, comprising ammonia, carbon dioxide and water, are condensed where after that formed concentrated process condensate is added via line (r) to the condensation section of the recovery section (REC).

Figure 2:
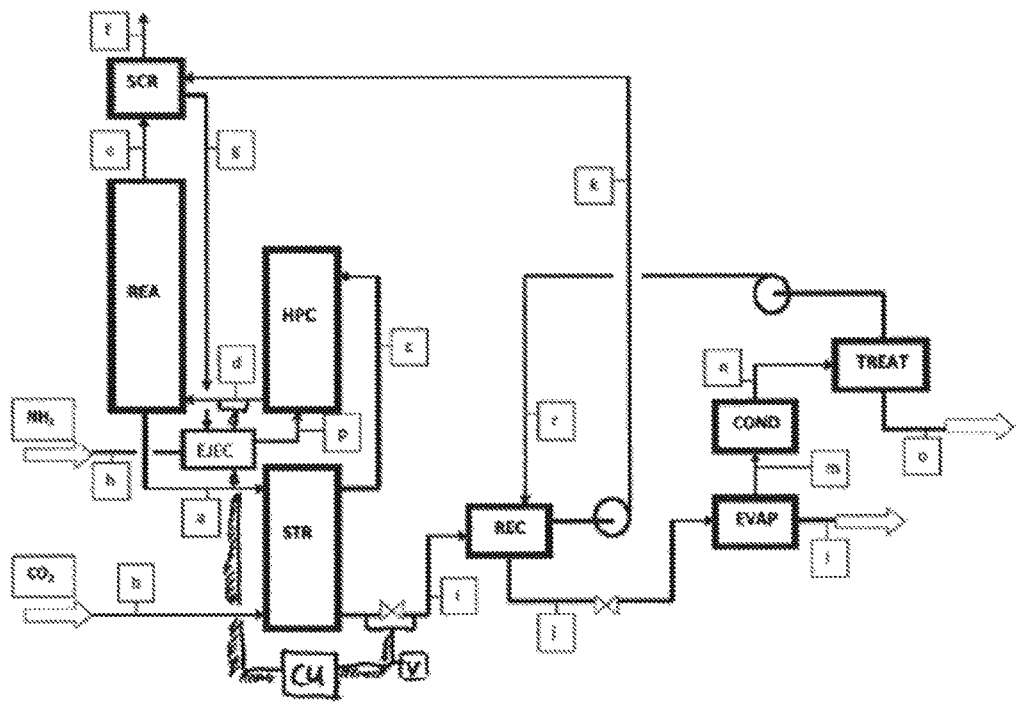
FIG. 2 shows a process scheme for a urea stripping process according to an embodiment of the invention, wherein the process of FIG. 1 is modified in accordance with the invention.

FIG. 2 shows a process scheme as in FIG. 1, modified in accordance with the invention. Accordingly, a compression unit (CU) is positioned downstream of the HP condenser and upstream of the reactor, whereby said compression unit is adapted to use energy recovered from the expansion of the liquid stream running via line (i) from the stripper to the recovery section. The energy recovery is indicated by shaded line (v). In a preferred embodiment (not shown in FIG. 2), the compression unit (CU) and the pressure reduction valve associated with line v, will be replaced by an energy recovery system, particularly comprising the compression unit as well as a decompression unit integrated in the form of an energy-recovery unit.

Figure 3:
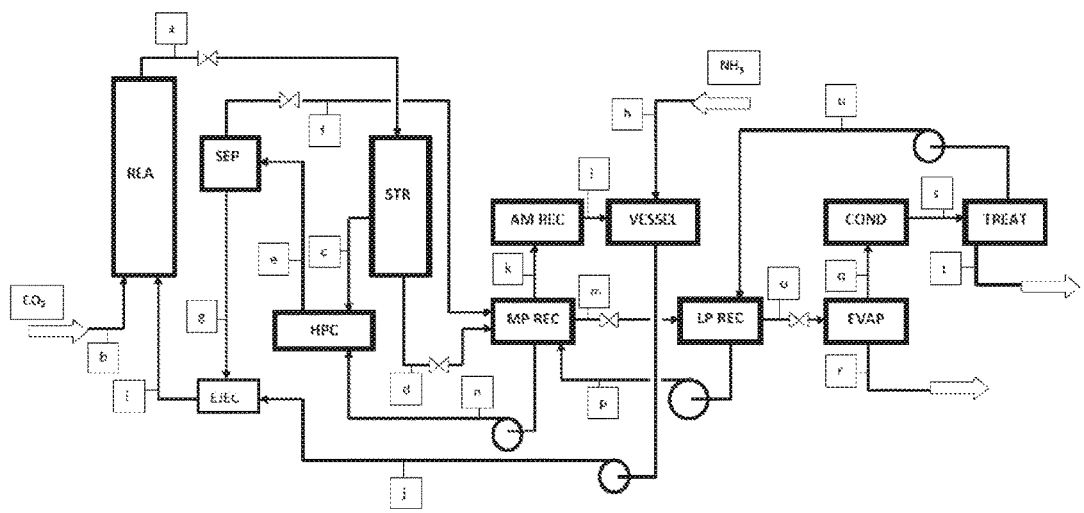
FIG. 3 shows a process scheme for a urea stripping process according to prior art wherein heat stripping is used.

FIG. 3 shows a typical heat stripping process known in the art. The synthesis section comprises typically the equipment: a reactor (REA), a stripper (STR), a condenser (HPC), an ejector (EJEC) and a liquid/gas separator (SEP). The reaction zone (REA) in the synthesis section is typically operated at a pressure in between 15 and 19 MPa while the pressure in the reactor (REA) is typically 0.3 to 1.2 MPa higher than the pressure in the remaining synthesis equipment. The pressure difference is realized by the application of an ejector (EJEC) that boosts the ammonium carbamate solution, formed in the condenser (HPC). The condenser (HPC) is typically a kettle type and since the tube side is the process side in this condenser, is the retention limited and as a consequence is the formed urea in such a condenser negligible. As driving force pressurized ammonia is used in the ejector (EJEC).

In the synthesis section the urea solution leaving the urea reactor (REA) is typically controlled at an ammonia to carbon dioxide molar ratio in between 3.1 and 3.9 mol/mol and the water to carbon dioxide molar ratio in the urea solution leaving the reactor (REA) is typically in the range of 0.5 to 0.7 mol/mol and usually in the range of 0.55 to 0.65 mol/mol. This urea solution is fed to a stripper (STR) in which a large amount of non-converted ammonia and carbon dioxide is separated from the aqueous urea solution. The stripper is a shell and tube heat exchanger in which the urea solution is fed to the top part via line (a) at the tube side. At the shell side of said stripper steam at a pressure of 1.0 to 2.3 MPa is added as a heating agent. The released vapor leaving the stripper (STR) via line (c) is sent to the condenser (HPC) together with the ammonium carbamate solution formed in the downstream recovery section (MP REC) via line (n). In this condenser (HPC) the exothermic ammonium carbamate reaction takes place. The released condensation heat is used to form steam that is used as heating agent and driving force of ejectors in the downstream processing of the synthesis section. The formed ammonium carbamate solution together with non-condensed ammonia and carbon dioxide vapor is sent via line (e) to a vessel (SEP) in which the vapor phase is separated from the ammonium carbamate liquid phase. The ammonium carbamate solution is sent via line (g) to an ejector where the discharged ammonium carbamate solution is increased in pressure in between 0.3 to 1.2 MPa. As a driving force pressurized liquid ammonia (j) is used. The pressurized ammonium carbamate solution enters the reactor (REA) via line (i) together with the feedstock carbon dioxide via line (b). In the reactor (REA) the endothermic urea reactor proceeds approaching the chemical equilibrium. The urea solution comprising urea, ammonia, carbon dioxide and water together with the non-condensed vapor comprising ammonia, carbon dioxide and inerts leave the reactor (REA) via line (a). In this line (a) the urea solution is expanded by a valve to a pressure that is in the range of 0.3 to 1.2 MPa lower than the pressure in the reactor (REA). Said urea solution together with the non-condensed and expanded vapor enters the stripper (STR) at the top side.

The stripped urea solution leaving the stripper (STR) at the bottom via line (d) comprises typically 6 to 10% by weight of non-converted carbon dioxide and is expanded and subsequently added to a first recovery section (MP REC) operated at a pressure in the range of 1.5 to 2.5 MPa. The non-condensed vapor leaving the synthesis section via line (f) is added to the first recovery section (MP REC) as well. In this first recovery section (MP REC) the excess of ammonia is separated from the urea and ammonium carbamate solution. The excess ammonia in the vapor phase leaves the first recovery section via line (k) to the ammonia recovery section (AM REC) in which the ammonia vapor is condensed (l) after which it is collected in an ammonia collection vessel (VESSEL). The feedstock ammonia liquid from battery limit is added to this vessel (VESSEL) as well, via line (h), after which the liquid ammonia via line (j) is increased in pressure and used as driving force for the ejector (EJEC) in the synthesis section.

The ammonium carbamate left in the urea solution is heated in a decomposer in the first recovery section (MP REC) to separate the ammonia and carbon dioxide from the urea solution. The vapor formed in said decomposer comprises ammonia and carbon dioxide and is subjected to condensation to form an ammonium carbamate solution that leaves the first recovery section (MP REC) via line (n). This ammonium carbamate solution is increased in pressure where after it is added to the condenser (HPC) in the synthesis section.

The urea solution leaving the first recovery section (MP REC) via line (m) is expanded and thereafter added to a second recovery section (LP REC) typically operated at a pressure in the range of 0.2 to 0.6 MPa. This urea solution leaving the first recovery section (MP REC) still contains a considerable amount of ammonia and carbon dioxide. The second recovery section (LP REC) comprises usually a decomposer and a condensation. The decomposer is usually a shell and tube heat exchanger. In the decomposer the ammonium carbamate left in the urea solution is fed to the tube side and decomposed into ammonia and carbon dioxide vapor by adding steam to the shell side. The urea solution leaves said decomposer at a temperature of 120-145° C. and preferably at a temperature of 130-140° C. where after the pressure of said urea solution is decreased causing a further purification of the urea solution by flashing.

The released vapor from the decomposer comprising ammonia, carbon dioxide and water is condensed in the condensation section of this recovery section (LP REC) thereby forming an ammonium carbamate solution that is pumped to preferably the condensation in the first recovery section (MP REC) via line (p).

The urea solution leaving the second recovery section (LP REC) arrives via line (o) the evaporation section (EVAP). In this evaporation section (EVAP) the urea solution is concentrated to the desired urea concentration that is determined by the finishing section (not indicated). Usually the concentration of the urea solution takes place at sub-atmospheric pressure and dependent of the required concentration one or a plurality of evaporators are used. The concentrated urea solution leaves the evaporation section via line (r). The released vapor leaving the evaporators via line (q) comprising water, ammonia and carbon dioxide is condensed to form process condensate. Since the operation pressure in the evaporator is sub-atmospheric, small amounts of urea is entrained and leaves the evaporators via the vapor phase (q). This urea is traced back in the formed process condensate leaving the condensation section (COND) via line (s). Said formed process condensate is thereafter totally or partially being used as absorbent in the absorbers of the plant to purify inert vapor, subjected to a process condensate treatment section (TREAT). The process condensate treatment section comprises a first desorber, a hydrolyser column or horizontal vessel followed by a next second desorber. In the first desorber the bulk of ammonia and carbon dioxide is stripped from the water solution. The stripped condensate is subjected to a heated liquid filled column/vessel (hydrolyser) in which the urea, occurring in said condensate, is decomposed into ammonia and carbon dioxide. The effluent leaving this hydrolyser comprising water, ammonia and carbon dioxide is subjected to the next second desorber in which the left ammonia and carbon dioxide is stripped from the condensate. Usually steam is used as stripping agent in this second desorber. The purified process condensate leaves the treatment section (TREAT) via line (t). The hot off gas leaving the second desorber comprising ammonia and carbon dioxide is usually used as stripping agent for the said first desorber. The off gases leaving the first desorber, comprising ammonia, carbon dioxide and water, are condensed where after that formed concentrated process condensate is pumped via line (u) to the condensation section of the recovery section (LP REC).

Figure 4:
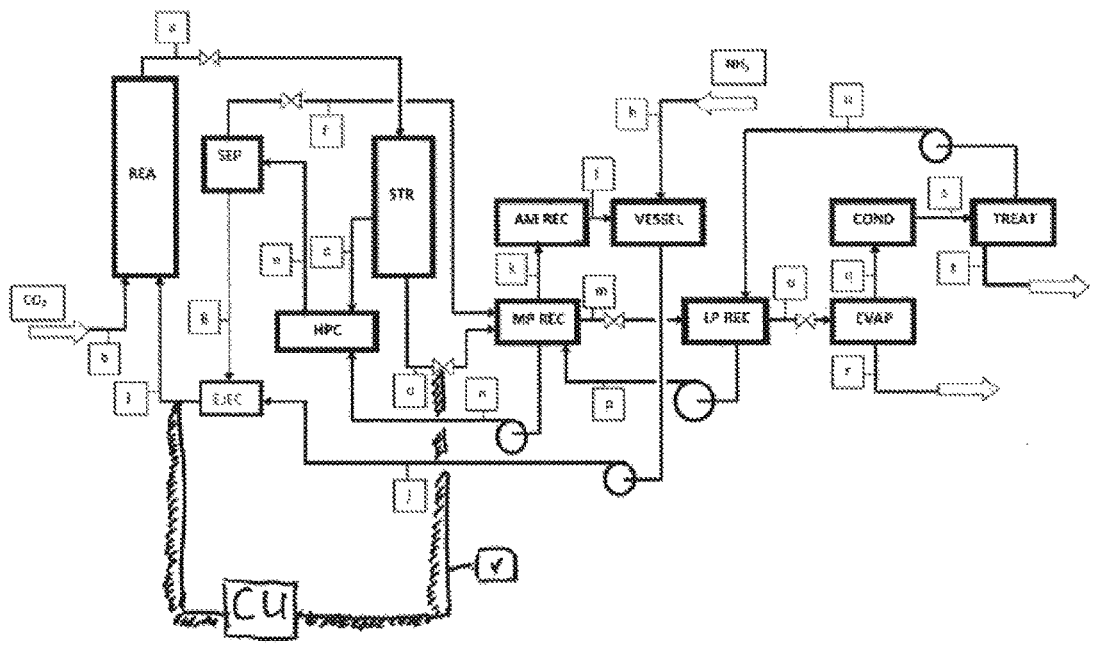
FIG. 4 shows a process scheme for a urea stripping process according to an embodiment of the invention, wherein the process of FIG. 3 is modified in accordance with the invention.

FIG. 4 shows a process scheme as in FIG. 3, modified in accordance with the invention. Accordingly, a compression unit (CU) is positioned downstream of the HP condenser and upstream of the reactor, whereby said compression unit is adapted to use energy recovered from the expansion of the liquid stream running via line (i) from the stripper to the recovery section. The energy recovery is indicated by shaded line (v). As mentioned above, in a preferred embodiment (not shown in FIG. 4), the compression unit CU and the pressure reduction valve associated with line v, will be replaced by an energy recovery system, particularly comprising the compression unit as well as a decompression unit integrated in the form of an energy-recovery unit.

Figure 5:
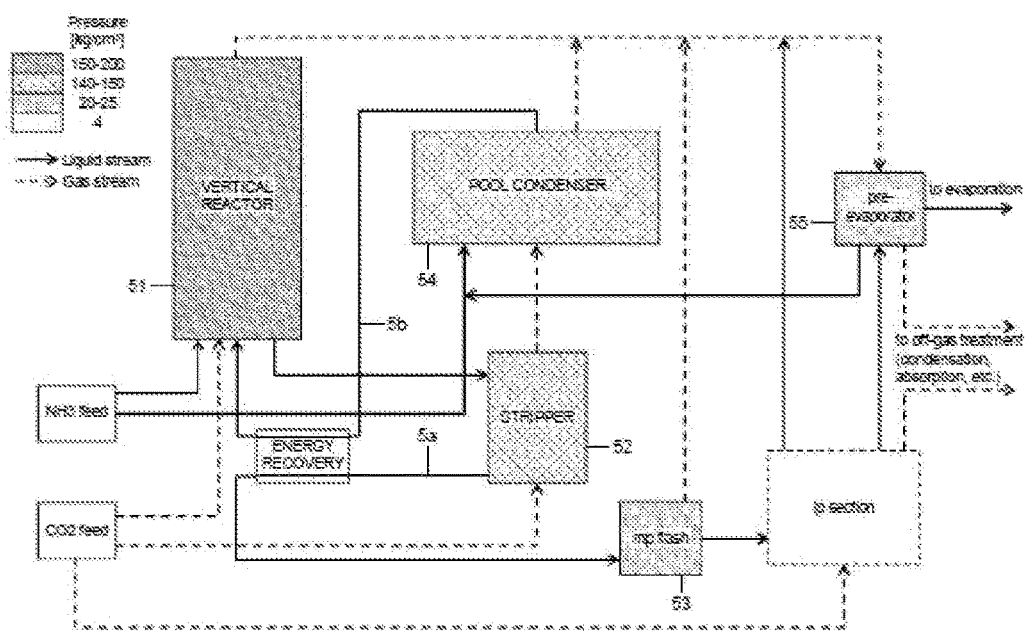
FIG. 5 shows a process scheme for a urea stripping process according to an embodiment of the invention, wherein a MP-flash is included.

FIG. 5 shows a process scheme for a urea stripping process according to an embodiment of the invention, wherein a MP-flash is included. A high-pressure reactor (16 MPa-20 MPa) (51) fed with carbon dioxide and ammonia to form a urea solution and a gas stream. The urea solution is sent to a high-pressure (13 MPa-15 MPa) CO2 stripper (52) wherein a product stream and an ammonia and CO2 containing gas stream are formed. The product stream is sent to a medium-pressure recovery section (2 MPa-2.5 MPa) (53) and the aforementioned ammonia and $CO_2$ containing gas stream is sent to the high-pressure pool condenser (13 MPa-15 MPa) (54). Additionally, an ammonia feed that could be pre-heated, together with recycled ammonium carbamate, is sent to the reactor. The liquid stream leaving the pool condenser is directed to the high-pressure reactor; the gas stream leaving the pool condenser is collected together with the gas stream from the high-pressure reactor and with the ammonia and CO2 containing gas leaving the medium and low-pressure recovery section to a pre-evaporator (2 MPa-2.5 MPa) (55). The system comprises an energy-recovery unit (56) configured to obtain energy from liquid pressure reduction (stream 5a, running from the high pressure stripper to the medium pressure treatment section), so as to increase the pressure of liquid sent from the high pressure condenser to the reactor (stream 5b).

In sum, the invention relates to a urea plant wherein, in deviation from conventional plants, a high-pressure synthesis section is operated with two different pressures. The synthesis section comprises a reactor, which is operated under a first high pressure. The synthesis section also comprises a stripper and a condenser, both operated at substantially the same second high pressure. In accordance with the invention, the first pressure is substantially higher than the second pressure. The disclosed plant particularly comprises a compression unit capable of converting a pressure difference into mechanical energy. This compression unit is positioned between the liquid outlet of the condenser and the liquid inlet of the reactor, and in fluid communication therewith. In order to make use of a pressure drop (expansion as a result of a liquid being depressurized), said compression unit is configured to obtain compression energy from one or more events in the urea production process (i.e., at one or more points in the urea production plant), at which a loss of energy occurs, such as decompression of a high energy stream. Typically, the compression unit is thereby configured to utilize mechanical energy recovered from a decompression unit positioned downstream of the stripper and upstream of the recovery section.

The invention claimed is:

1. A plant for the production of urea comprising a synthesis section configured to be operated under a high pressure between 12 and 40 MPa and a recovery section configured to be operated under a pressure below 7 MPa, said synthesis section comprising, connected so as to be capable of forming a urea synthesis loop, a urea reactor, a stripper, a condenser and, optionally, a scrubber, wherein the synthesis section is configured so as to allow the reactor to be operated under a pressure substantially higher than the pressure of the stripper and the condenser, and wherein the synthesis section comprises a compression unit positioned downstream of the condenser and upstream of the reactor, said compression unit being configured so as to increase the pressure of fluid, obtained from the condenser to substantially the same pressure under which the reactor is operated, whereby said compression unit is configured to utilize mechanical energy recovered from a decompression unit positioned downstream of the stripper and upstream of the recovery section.

2. The plant of claim 1, wherein the decompression unit and the compression unit are integrated in the form of an energy-recovery unit.

3. The plant of claim 2, wherein the decompression unit and the compression unit share a common rotating axis configured to be driven by liquid depressurization energy obtained from the decompression unit.

4. The plant of claim 1, said plant being a carbon dioxide stripping plant, wherein the stripper is capable of being operated using carbon dioxide as a stripping gas.

5. The carbon dioxide stripping plant of claim 4, adapted so as to feed additional carbon dioxide directly to the reactor.

6. The plant of claim 1, wherein the synthesis section is configured to be operated with a pressure difference such that the reactor is operated at a pressure of at least 0.5MPa higher than the pressure of the stripper and the condenser, and up to 80 MPa higher.

7. The plant of claim 6, wherein said pressure difference is in a range of from 2 MPa to 5 MPa.

8. The plant of claim 1, wherein the stripper and the condenser are adapted to be operated under a pressure of from 13 to 15 MPa, and the reactor is adapted to be operated under a pressure of 16 to 21 MPa.

9. The plant of claim 1, wherein the condenser is a submerged condenser.

10. The plant of claim 1, wherein the reactor is placed at a low level such that the liquid inlet of the reactor for receiving condensate from the condenser, is below the outlet of the condenser for said condensate.

11. The plant of claim 1, wherein the reactor is positioned vertically.

12. The plant of claim 1, comprising a medium pressure treatment section downstream of the reactor and upstream of the recovery section.

13. A method of modifying a pre-existing urea stripping plant so as to provide a modified plant, said pre-existing plant comprising a synthesis section adapted to operate under a high pressure between 12 and 40 MPa and a recovery section adapted to operate under a pressure below 7 MPa, said synthesis section comprising, connected so as to be capable of forming a urea synthesis loop, a urea reactor, a stripper, a condenser and optionally a scrubber, wherein the modifying of the pre-existing plant comprises adding a compression unit in a position downstream of the HP condenser and upstream of the reactor, wherein the synthesis section is configured so as to allow the reactor to be operated under a pressure substantially higher than the pressure of the stripper and the condenser, said compression unit being adapted so as to increase the pressure of fluid, obtained from the HP condenser to substantially the same pressure under which the reactor is operated, whereby said compression unit is configured to utilize mechanical energy recovered from decompression of liquid downstream of the stripper and upstream of the recovery section.

14. A method of modifying a pre-existing urea recycle plant so as to provide a modified plant, said pre-existing plant comprising, placed in series, a HP reactor adapted to be operated at a high pressure of 16 to 40 MPa so as to obtain a urea synthesis solution, a MP recirculation section adapted to be operated at a medium pressure of 1 to 5 MPa, and an LP recirculation section adapted to be operated at a low pressure of 0.1 to 1 MPa, said recirculation sections adapted to decompose ammonium carbamate and to recirculate a liquid condensate comprising non-reacted carbon dioxide and ammonia, and liquid components comprising ammonium carbamate, back to the reactor, the method comprising:

adding a HP stripper downstream of the reactor and upstream of the MP recirculation section, said stripper being adapted so as to direct liquid obtained therefrom to either or both of the MP and LP recirculation sections;

adding a HP condenser, whereby the HP condenser and the HP stripper are mutually arranged to subject gas obtained from the HP stripper to condensation in said HP condenser so as to form a liquid condensate and remaining vapors;

arranging said HP condenser in connection with a compression unit positioned downstream of the condenser and upstream of the reactor wherein said compression unit is configured so as to increase the pressure of liquid condensate, obtained from the condenser, to substantially the same pressure under which the reactor is operated, whereby said compression unit is configured to utilize mechanical energy recovered from decompression of liquid downstream of the stripper and upstream of the recovery section.

15. The method of claim 13, wherein the modified plant comprises a synthesis section configured to be operated under a high pressure between 12 and 40 MPa and a recovery section configured to be operated under a pressure below 7 MPa, said synthesis section comprising, connected so as to be capable of forming a urea synthesis loop, a urea reactor, a stripper, a condenser and, optionally, a scrubber, wherein the synthesis section is configured so as to allow the reactor to be operated under a pressure substantially higher than the pressure of the stripper and the condenser, and wherein the synthesis section comprises a compression unit positioned downstream of the condenser and upstream of the reactor, said compression unit being configured so as to increase the pressure of fluid, obtained from the condenser to substantially the same pressure under which the reactor is operated, whereby said compression unit is configured to utilize mechanical energy recovered from a decompression unit positioned downstream of the stripper and upstream of the recovery section.

16. A process for the preparation of urea in a urea production plant, said plant comprising a synthesis section operating under a high pressure between 12 and 40 MPa and a recovery section operating under a pressure below 1 MPa, said synthesis section comprising, connected so as to be capable of forming a urea synthesis loop, a urea reactor, a stripper, a condenser and optionally a scrubber, the process comprising the steps of:
   a) reacting ammonia and $CO_2$ under urea forming conditions in the urea reactor to obtain a urea synthesis solution;
   b) stripping the urea synthesis solution in the stripper to form a stripped urea solution and a stripper vapor comprising ammonia, $CO_2$ and water;
   c) condensing the stripper vapor obtained in b) in the condenser to form an ammonium carbamate solution;
   d) recirculating said ammonium carbamate solution to the reactor;
   e) subjecting the stripped urea solution to recovery of ammonia, and optionally $CO_2$, in the recovery section to obtain a urea product solution and a recovery vapor comprising the ammonia and the optional $CO_2$;
   f) recycling the recovery vapor to the urea synthesis section;
   the process further comprising operating the urea reactor under a pressure at least 2 MPa higher pressure than the pressure of the stripper and the condenser, and increasing the pressure of the ammonium carbamate solution upon recirculation to the reactor, wherein energy utilized in increasing said pressure comprises mechanical energy recovered from a decompression unit positioned downstream of the stripper and upstream of the recovery section.

17. The process of claim 16, wherein the urea synthesis is conducted in a plant that comprises a synthesis section configured to be operated under a high pressure between 12 and 40 MPa and a recovery section configured to be operated under a pressure below 7 MPa, said synthesis section comprising, connected so as to be capable of forming a urea synthesis loop, a urea reactor, a stripper, a condenser and, optionally, a scrubber, wherein the synthesis section is configured so as to allow the reactor to be operated under a pressure substantially higher than the pressure of the stripper and the condenser, and wherein the synthesis section comprises a compression unit positioned downstream of the condenser and upstream of the reactor, said compression unit being configured so as to increase the pressure of fluid, obtained from the condenser to substantially the same pressure under which the reactor is operated, whereby said compression unit is configured to utilize mechanical energy recovered from a decompression unit positioned downstream of the stripper and upstream of the recovery section.

18. The plant of claim 1, comprising a flow line from an outlet of said urea reactor to an inlet of said stripper, wherein said flow line comprises a pressure control valve so as to reduce the pressure of a urea solution supplied from said urea reactor to said stripper.

19. The plant of claim 1 wherein the compression unit is configured so as to increase the pressure of liquid condensate obtained from the condenser to substantially the same pressure under which the reactor is operated.

20. The method of claim 13 wherein the compression unit is configured so as to increase the pressure of liquid condensate obtained from the condenser to substantially the same pressure under which the reactor is operated.

* * * * *